(12) United States Patent
Roberts

(10) Patent No.: US 12,256,946 B2
(45) Date of Patent: Mar. 25, 2025

(54) SURGICAL RONGEUR AND METHODS THEREOF

(71) Applicant: Timothy Tian Roberts, New York, NY (US)

(72) Inventor: Timothy Tian Roberts, New York, NY (US)

( * ) Notice: Subject to any disclaimer, the term of this patent is extended or adjusted under 35 U.S.C. 154(b) by 699 days.

(21) Appl. No.: 17/538,492

(22) Filed: Nov. 30, 2021

(65) Prior Publication Data

US 2022/0167994 A1   Jun. 2, 2022

Related U.S. Application Data

(60) Provisional application No. 63/119,581, filed on Nov. 30, 2020.

(51) Int. Cl.
*A61B 10/02*   (2006.01)
*A61B 17/16*   (2006.01)
*A61B 17/32*   (2006.01)
*A61B 17/00*   (2006.01)

(52) U.S. Cl.
CPC ........ *A61B 17/1608* (2013.01); *A61B 10/025* (2013.01); *A61B 10/0266* (2013.01); *A61B 17/32* (2013.01); *A61B 2017/00376* (2013.01); *A61B 17/1604* (2013.01); *A61B 17/1611* (2013.01); *A61B 2017/320064* (2013.01)

(58) Field of Classification Search
CPC .... A61B 17/1611; A61B 2017/320064; A61B 2010/0225; A61B 17/1671; A61B 17/1608; A61B 2017/00376; A61B 10/0266; A61B 10/025; A61B 2010/0258; A61B 17/1606; A61B 17/1635; A61B 17/32053; A61B 17/1604; A61B 10/0096; A61B 10/04; A61B 10/02; A61B 17/56; A61B 10/0233
See application file for complete search history.

(56) References Cited

U.S. PATENT DOCUMENTS

| | | | | |
|---|---|---|---|---|
| 5,385,570 A | * | 1/1995 | Chin | A61B 17/1611 600/564 |
| 5,569,258 A | * | 10/1996 | Gambale | A61B 17/1611 606/171 |
| 5,573,008 A | * | 11/1996 | Robinson | A61B 10/0266 600/567 |
| 5,681,337 A | * | 10/1997 | Bray, Jr. | A61B 17/1611 606/83 |
| 5,683,406 A | * | 11/1997 | Altobelli | A61B 17/32 30/317 |

(Continued)

*Primary Examiner* — Shaun L David
*Assistant Examiner* — Mitchell Brian Hoag

(57) ABSTRACT

A surgical rongeur includes a lower shaft that defines a floor including a trap door, the lower shaft terminates in a static footplate. An upper shaft is slidably coupled to a top surface of the lower shaft, the upper shaft terminates in a cutting blade. An elongated member is slidably coupled along the floor of the lower shaft and terminates in a sliding footplate. A primary trigger is coupled to the upper shaft, where actuation of the primary trigger is configured to alternately move the cutting blade between an open position and a closed position. A secondary trigger is coupled to the elongated member, where actuation of the secondary trigger, while the cutting blade is in the closed position, is configured to retract the sliding footplate from the static footplate into one of a plurality of positions.

20 Claims, 18 Drawing Sheets

(56) References Cited

U.S. PATENT DOCUMENTS

| | | | | |
|---|---|---|---|---|
| 5,766,177 | A * | 6/1998 | Lucas-Dean | A61B 17/1611 606/184 |
| 6,261,294 | B1 * | 7/2001 | Stihl | A61B 17/1611 606/83 |
| 9,005,239 | B2 * | 4/2015 | Seel | A61B 17/2816 606/208 |
| 9,168,046 | B2 * | 10/2015 | Weisshaupt | A61B 17/1611 |
| 10,507,027 | B2 * | 12/2019 | Fetzer | A61B 17/1611 |
| 2005/0267503 | A1 * | 12/2005 | Hunstad | A61B 17/1671 606/170 |
| 2006/0064102 | A1 * | 3/2006 | Ebner | A61B 17/1659 606/84 |
| 2006/0189995 | A1 * | 8/2006 | Lancial | A61B 17/1611 606/83 |
| 2010/0179557 | A1 * | 7/2010 | Husted | A61B 17/32002 600/300 |
| 2013/0006249 | A1 * | 1/2013 | Paul | A61B 17/1604 606/83 |
| 2013/0041379 | A1 * | 2/2013 | Bodor | A61B 17/1611 606/83 |
| 2014/0039343 | A1 * | 2/2014 | Mescher | A61B 90/98 600/562 |
| 2015/0305820 | A1 * | 10/2015 | Salehi | A61B 17/1611 606/83 |
| 2016/0045190 | A1 * | 2/2016 | Elfman | A61B 10/04 600/567 |
| 2016/0081678 | A1 * | 3/2016 | Kappel | A61B 10/06 600/567 |
| 2016/0143632 | A1 * | 5/2016 | Hibner | A61B 10/0266 600/567 |
| 2017/0265881 | A1 * | 9/2017 | O'Neil | A61B 17/32 |
| 2019/0150952 | A1 * | 5/2019 | Kurd | A61B 17/1611 |
| 2020/0330105 | A1 * | 10/2020 | Bornhoft | A61B 90/03 |

* cited by examiner

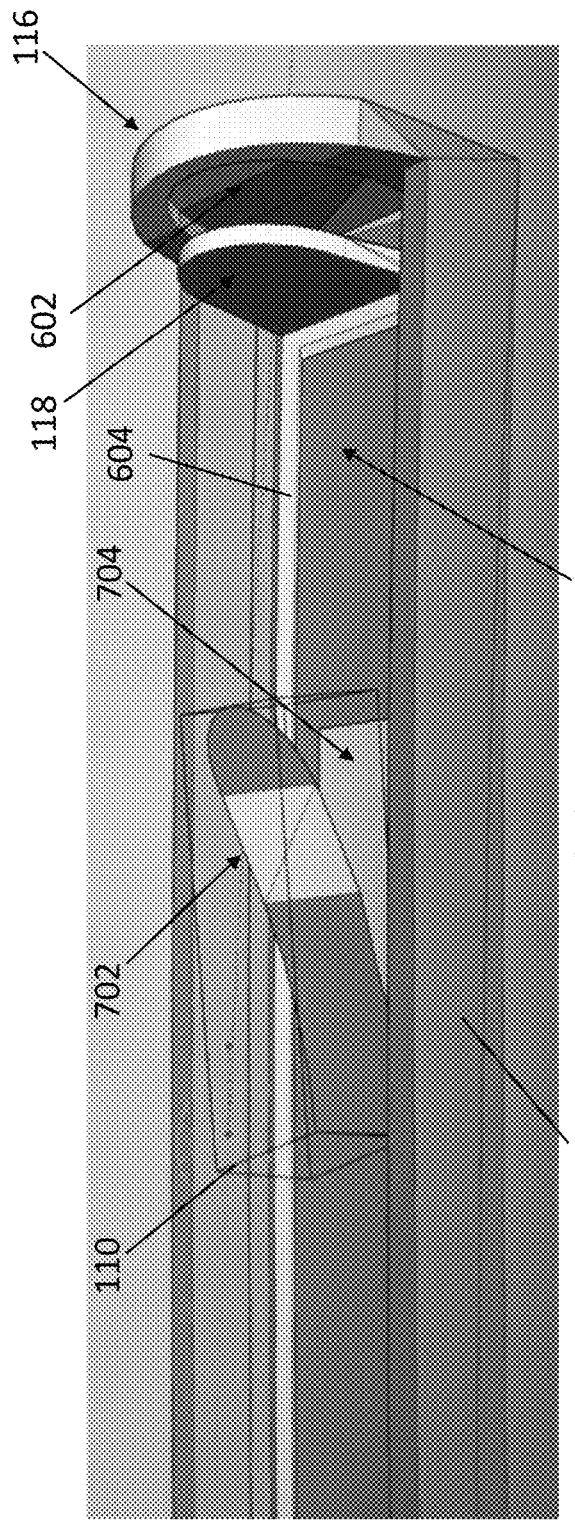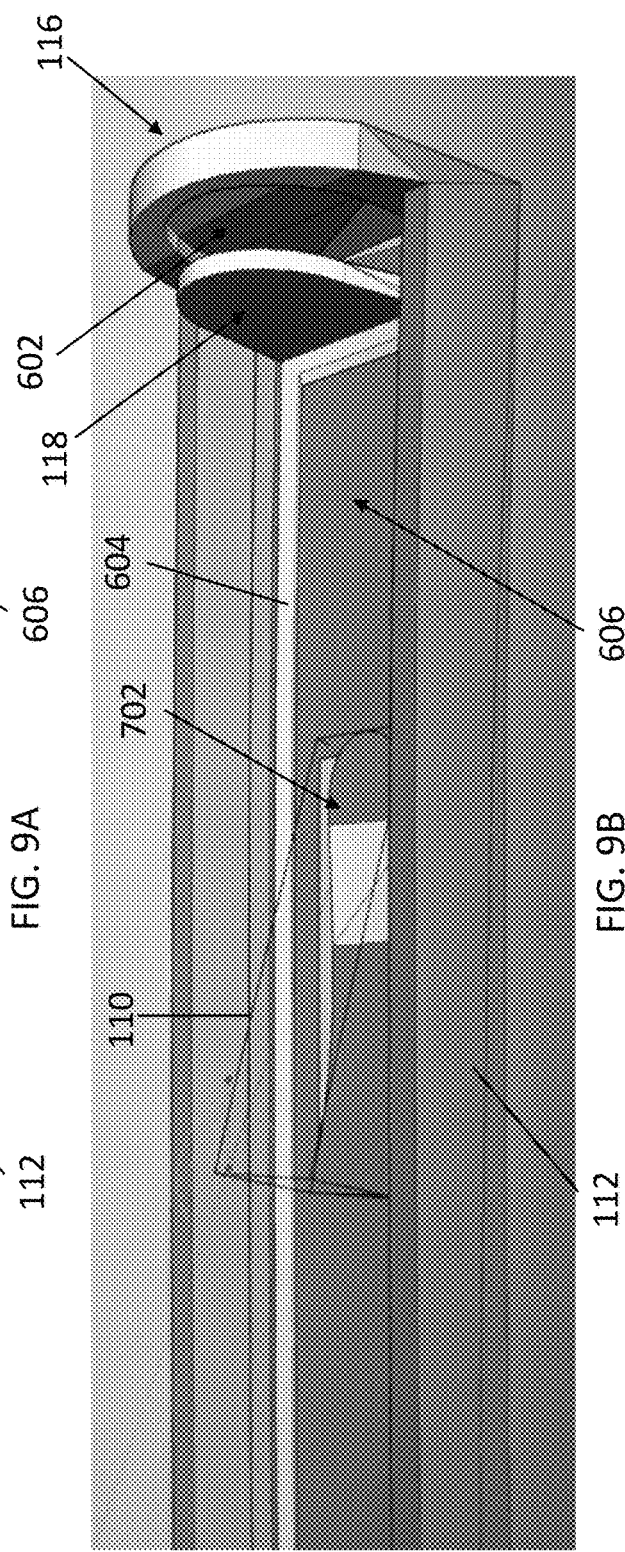
FIG. 9A
FIG. 9B

SURGICAL RONGEUR AND METHODS THEREOF

CROSS-REFERENCE TO RELATED APPLICATION

This application claims the benefit of U.S. Provisional Application No. 63/119,581, filed Nov. 30, 2020, the entirety of which is incorporated by reference herein.

BACKGROUND

A Kerrison rongeur is a surgical tool for removing "punches" of bone and other tissues during spinal surgery. In general, the Kerrison rongeur takes only a single bite of material (e.g., bone or other tissue) at a time and typically needs to be removed from the body, wiped clean, and returned to the body before another bite can be made. When performed dozens of times during even a small surgery, there is substantial time wasted cleaning and maneuvering the instrument. Moreover, multiple reentries and repositioning of the device substantially increases the risk of injury to neurological and other vulnerable structures, as well as raising the risk of wound contamination.

Thus, existing rongeurs have not proved entirely satisfactory in all respects.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIG. 9A and FIG. 9B illustrate additional views of the rongeur of FIG. 1, showing actuation of the trap door, in accordance with some embodiments;

DETAILED DESCRIPTION

Figure 1:
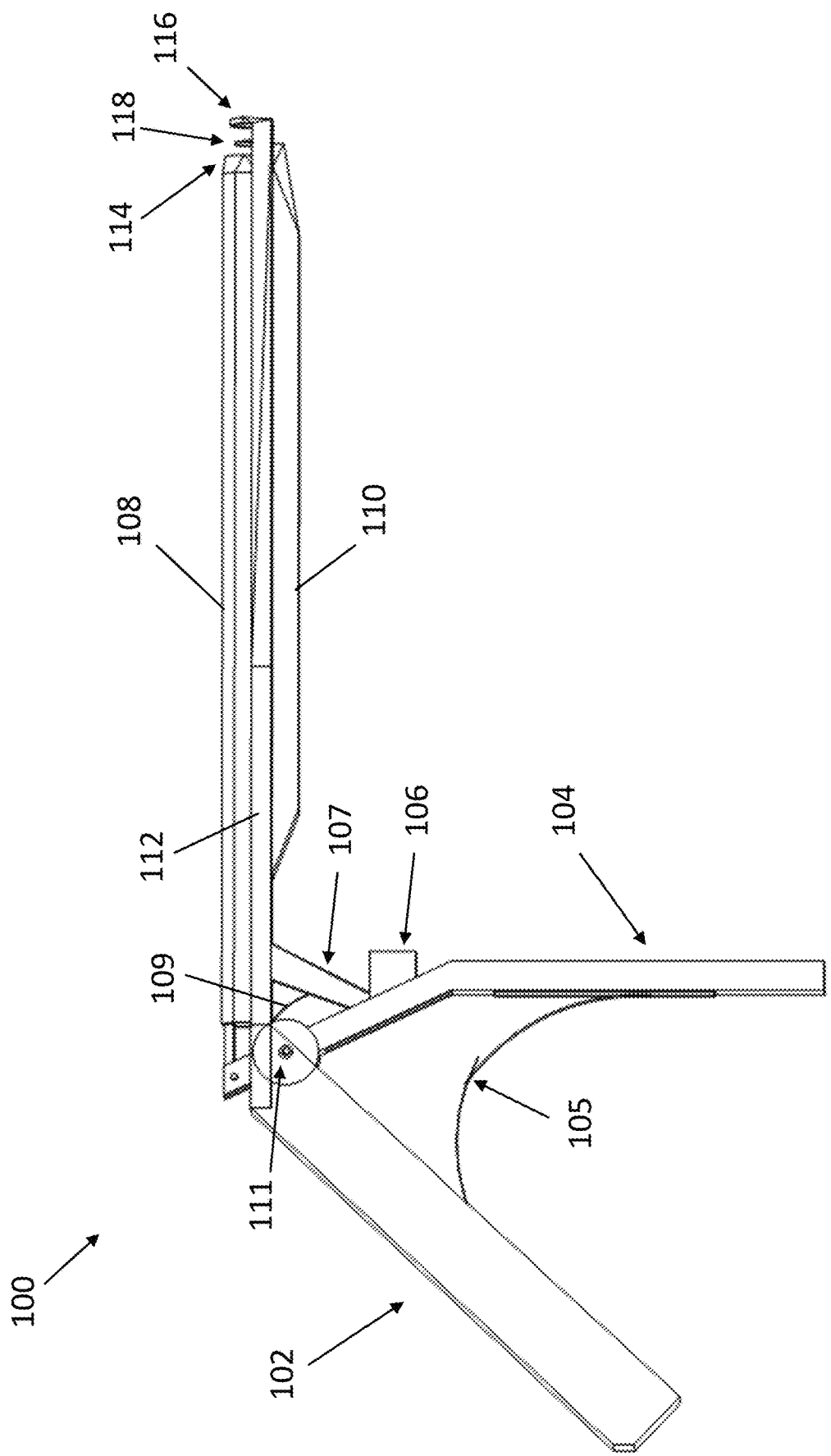
FIG. 1 illustrates a side view of a rongeur, in accordance with some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, a first element coupled to a second element in the description that follows may include embodiments in which the first and second elements are directly coupled, and may also include embodiments in which additional elements may be coupled between the first and second elements, such that the first and second elements may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

A Kerrison rongeur is a surgical tool for removing "punches" of bone and other tissues during spinal surgery (e.g., such as during a spinal nerve decompression surgery). Rongeurs are pistol-shaped tools with a solid handle and lower shaft, along which an upper shaft with a distal cutting blade can slide. This effectively acts like a single paper hole punch. A primary trigger is coupled to the upper shaft, and upon actuation of the primary trigger, the upper shaft slides distally to close the cutting blade over a static footplate. The "punched" bone or other tissue is then wiped from the mouth of the device and it can be reused. The Kerrison rongeur is one of the most common instruments used in spine surgery, and it plays a role in almost every kind of spinal nerve decompression procedure. With its blunt tip and side-cutting action, the instrument is over placed along nerves and other delicate tissues and is used to "bite" away constricting tissues, typically bone, spinal disc material, and ligaments that can effectively strangle the nerve. It is an adaptable and reliable tool, but it is not without some major shortcomings.

For example, because the rongeur generally takes only a single bite of material at a time, the rongeur typically needs to be removed from the body, wiped clean, and returned to the body dozens of times during the course of even a minor surgery. This results in a substantial amount of time being wasted cleaning and maneuvering the instrument. Moreover, many such reentries and repositioning of the instrument substantially increases patient risk (e.g., such as risk of injury to neurological and other vulnerable structures, as well as risk of wound contamination). In addition, during spinal fusions (spinal procedures in which removed fragments of bone are collected from the decompression portion of the procedure, processed, and returned to the body as self-donated bone graft) the surgeon must often specify (e.g., to a medical assistant) which rongeur contents to save and which to discard. This adds time and is a notoriously tedious part of such surgical procedures.

Embodiments of the present disclosure offer advantages over the existing art, though it is understood that other embodiments may offer different advantages, not all advantages are necessarily discussed herein, and no particular advantage is required for all embodiments. For example, embodiments of the present disclosure provide an improved surgical rongeur and related method that effectively addresses the shortcomings of existing rongeurs, such as described above. In various embodiments, the disclosed surgical rongeur provides for selectively saving or discarding bites of bone or other material. For purposes of this disclosure, the bites of bone or other material may be more generally referred to as "bites" or "bite contents". By way of example, and in addition to the primary trigger that actuates the upper shaft and distal cutting blade, various embodiments also include a secondary trigger coupled to an elongated member slidably coupled along a floor of the lower shaft of the rongeur. The elongated member terminates in a sliding footplate at the distal end of the elongated member. In some embodiments, the static footplate of the lower shaft includes a recess configured to receive the sliding footplate (e.g., while the secondary trigger is not actuated). In some examples, and while the primary trigger is actuated (e.g., such that the cutting blade bites bone or other material by contacting the static footplate), the secondary trigger may be pulled into one of multiple positions to selectively save or discard the bite contents. For example, pulling the secondary trigger into a first position (a "short pull") may retract the sliding footplate away from the static footplate such that the sliding footplate pushes the bite contents into a holding chamber defined within the upper shaft proximate to the cutting blade. In another example, pulling the secondary trigger into a second position (a "long pull") may retract the sliding footplate away from the static footplate such that the sliding footplate pushes the bite contents past the holding chamber and into a storage chamber defined within the upper shaft proximate to the holding chamber. The storage chamber may also include semi-rigid teeth to trap or store the bite contents therein.

After using the secondary trigger to push the bite contents into either the holding chamber or the storage chamber and releasing the secondary trigger (which is spring loaded), the sliding footplate may be returned to its default position within the recess of the static footplate. In some embodiments, the primary trigger may then be released to disengage the cutting blade such that the upper shaft slides backward (e.g., away from the static footplate) to reveal the "mouth" (e.g., bite opening) of the instrument. As the upper shaft slides backward to its default (open) position, it releases a spring-loaded trap door, defined within the lower shaft and disposed proximate to the distal end of the lower shaft, where the trap door opens upward from the floor of the lower shaft. In various embodiments, the trap door provides access to a waste chamber coupled to a bottom surface of the lower shaft. By way of example, when the primary trigger is released and the upper shaft slides back to its open position, the open trap door obstructs the path through the upper shaft (leading toward the storage chamber) and instead bite contents are ejected from within the holding chamber through the trap door. In some embodiments, the bite contents fall freely out of the trap door upon releasing the primary trigger. However, in some cases, the bite contents are forcefully ejected through the trap door by pressure applied on the bite contents by a spring coupled to an upper interior surface of the upper shaft within the holding chamber.

Alternatively, in some embodiments and after releasing the primary trigger, the secondary trigger may again be short pulled in order to forcefully eject the bite contents through the trap door (e.g., such as in cases where the bite contents are rubbery and/or sticky and require an additional nudge for complete ejection). In addition, and in various embodiments, the trap door may remain closed while the primary trigger is actuated, thereby preventing access to the waste chamber. Further, in some embodiments, a dedicated waste chamber need not be used, and instead bite contents may simply be ejected through the trap door and out of the rongeur. In still other embodiments, the roles of the storage chamber and the waste chamber may be reversed (e.g., the storage chamber may alternatively store waste material and the waste chamber may alternatively store bite contents that are to be saved). In some examples, the disclosed rongeur may be referred to as a "dual-chamber rongeur", where the upper shaft including the holding chamber and the storage chamber effectively defines a "first chamber", and where the waste chamber effectively defines a "second chamber". In embodiments where the roles of the storage chamber and the waste chamber are reversed, the upper shaft including the holding chamber and the waste chamber effectively defines the first chamber, and the waste chamber coupled to the bottom surface of the lower shaft defines the second chamber.

In various embodiments, the upper shaft with its hollow body and distal cutting blade is removable, thus providing a cost-effect method of (1) keeping the device sharp and functional while (2) decreasing the risk of cross-patient contamination as well as (3) facilitating cleaning of the reusable portion of the instrument. It should be noted that a variety of distal cutting blade sizes and shapes could be interchangeably used on the same non-disposable handle and lower shaft. In other words, in some embodiments the removable upper shaft with the cutting blade is disposable. The ability to interchangeably use a variety of upper shafts with different cutting blades may offer substantial cost advantages in comparison to at least some existing instruments which essentially feature up to a half-dozen of the same Kerrison rongeurs in different "jaw" or "bite" sizes. Additionally, in some embodiments, the upper shaft's distal cutting blades may be beveled inward (e.g., the perimeter of the leading edge being the narrow-most portion) to reduce the likelihood of jamming. Also, in some cases, the storage chamber itself may gradually expand as one moves proximally away from the cutting blade. This, too, would reduce the likelihood of jamming. Those skilled in the art will recognize other benefits and advantages of the methods and surgical rongeur as described herein, and the embodiments described are not meant to be limiting beyond what is specifically recited in the claims that follow.

Referring now to FIG. 1, illustrated therein is a side view of a rongeur 100, in accordance with some embodiments. In various embodiments, the rongeur 100 includes a lower shaft 112, an upper shaft 108 slidably and removably coupled to a top surface of the lower shaft 112. The rongeur 100 further includes a removable waste chamber 110 coupled to a bottom surface of the lower shaft 112. As shown, a handle 102 and a primary trigger 104 are coupled to a proximal end of the rongeur 100. In particular, the primary trigger 104 is coupled to a proximal end of the upper shaft 108 such that actuation of the primary trigger 104 causes the upper shaft 108 to slidably move from an open position to a closed position along the (static) lower shaft 112. In the closed position, a cutting blade 114 of the upper shaft 108 is configured to engage (contact) a static footplate 116 of the lower shaft 112 to remove bites of bone or other material. When the primary trigger 104 is actuated, movement of the upper shaft 108 into the closed position also serves to close a trap door defined within a floor of the lower shaft 112, described in more detail below, thereby blocking access to the waste chamber 110. By way of example, when the primary trigger 104 is released, a spring mechanism 105 coupled between the handle 102 and the primary trigger 104 causes the upper shaft 108 to slide back to its open position. In some embodiments, the rongeur 100 also includes a secondary trigger 106 configured to actuate a sliding footplate 118 to selectively save or discard bite contents, as described in more detail herein. More particularly, the secondary trigger 106 may be coupled (e.g., via a coupling member 107) to an elongated member (described below) that is slidably coupled along a floor of the lower shaft 112 of the rongeur 100. The elongated member terminates in the sliding footplate 118 at the distal end of the elongated member, and the static footplate 116 of the lower shaft 112 includes a recess configured to receive the sliding footplate 118, for example, when the sliding footplate 118 is in a resting position. The sliding footplate 118 may be in the resting position when the secondary trigger 106 is not actuated, and a spring 109 coupled between the coupling member 107 and a joint 111, causes the sliding footplate 118 to move into the resting position.

Figure 2:
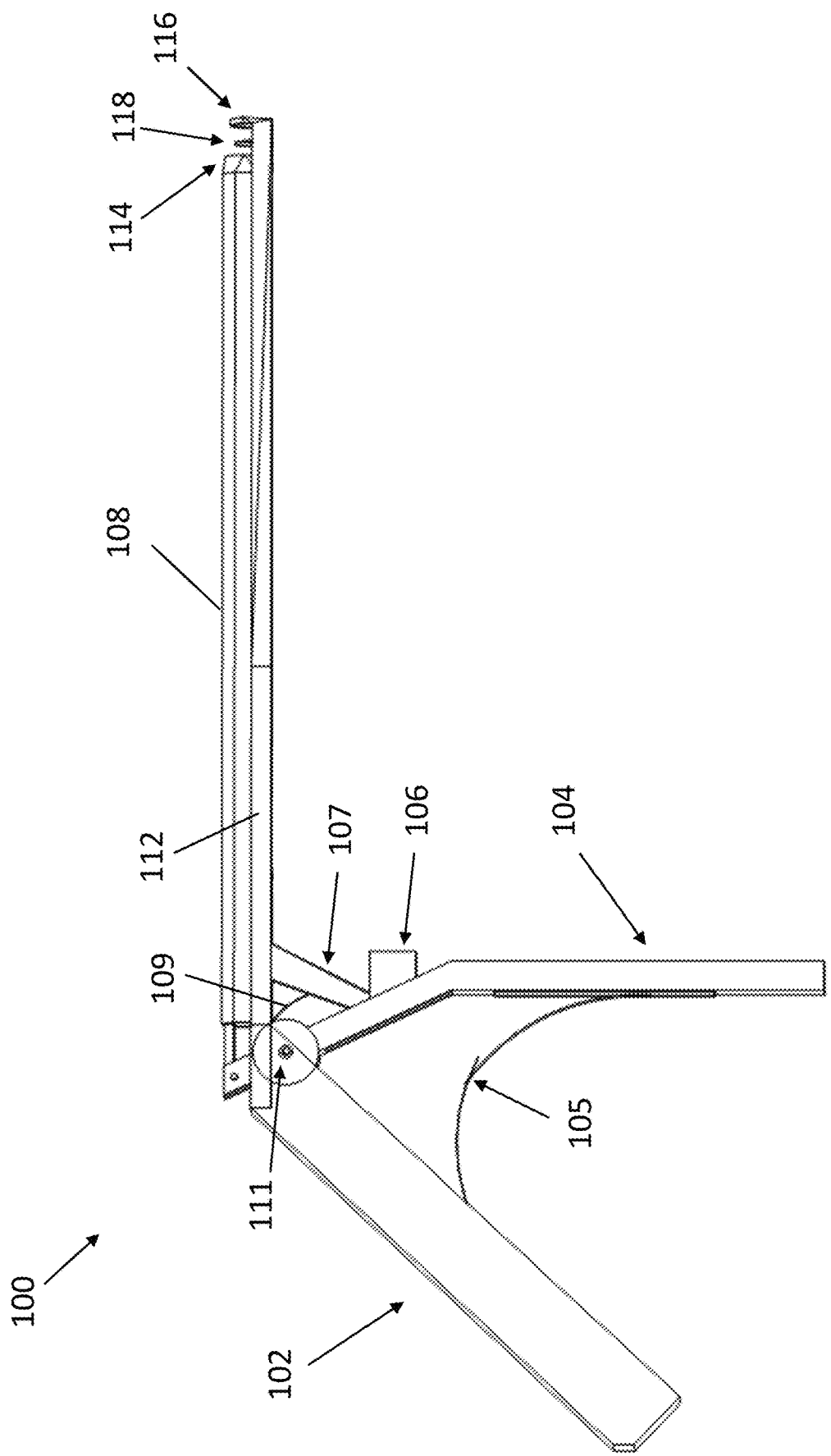
FIG. 2 illustrates an alternative embodiment of the rongeur of FIG. 1, in accordance with some embodiments.
Figure 3:
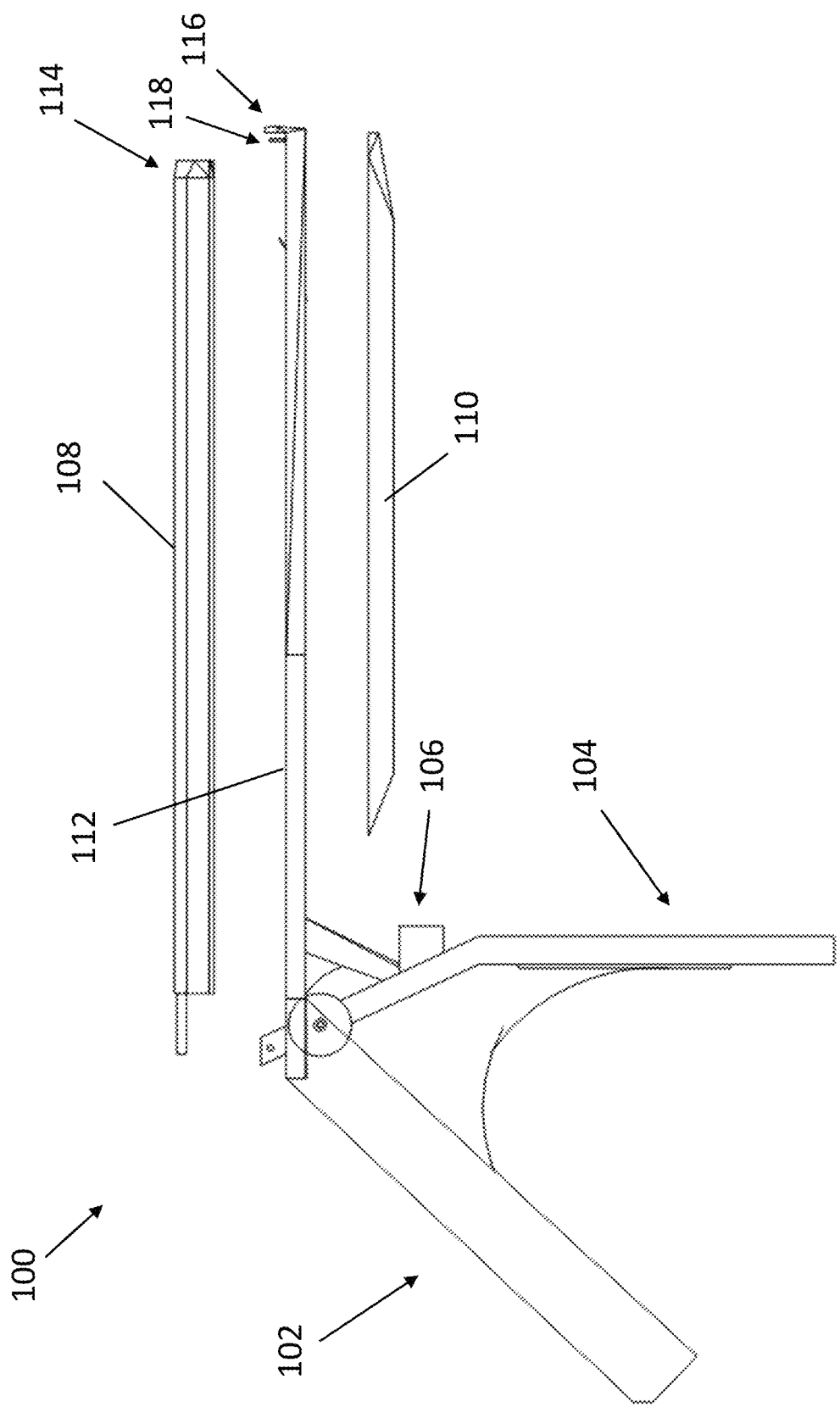
FIG. 3 illustrates a disassembled view of the rongeur of FIG. 1, in accordance with some embodiments.
Figure 4:
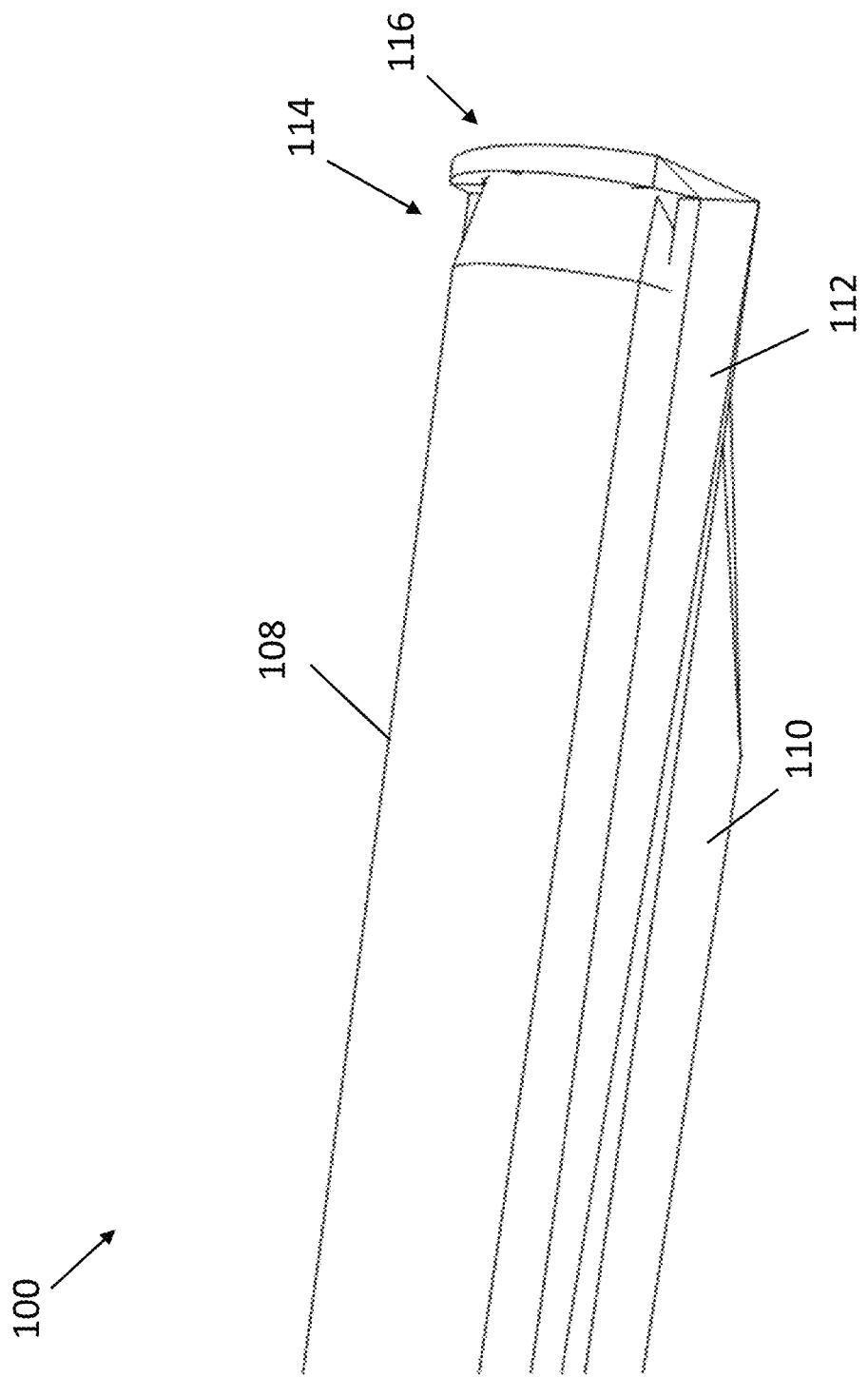
FIG. 4 and FIG. 5 illustrate a front portion of the rongeur of FIG. 1, in accordance with some embodiments.
Figure 5:
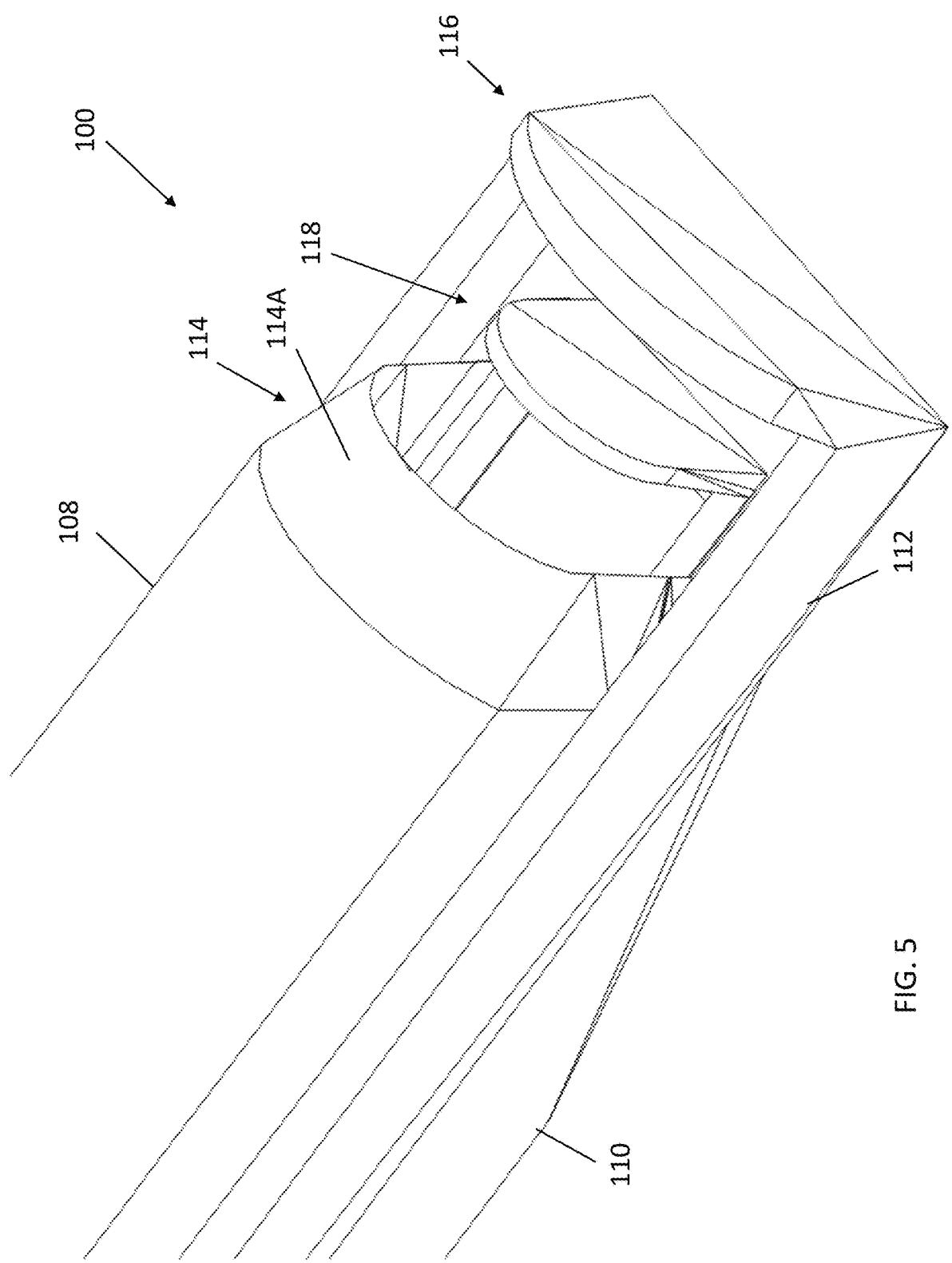

FIG. 2 illustrates another embodiment of the rongeur 100, as shown in FIG. 1, with the waste chamber 110 removed. As noted above, and in some embodiments, a dedicated waste chamber need not be used, and instead bite contents may simply be ejected through the trap door and out of the rongeur 100. The example of FIG. 3 illustrates a disassembled view of the rongeur 100 of FIG. 1, including the upper shaft 108, the lower shaft 112, the waste chamber 110, the handle 102, the primary trigger 104, the secondary trigger 106, the static footplate 116, and the sliding footplate 118. Referring to the example of FIG. 4, illustrated therein is a front portion of the rongeur 100 with the upper shaft 108 in the closed position, where the cutting blade 114 engages (contacts) the static footplate 116 of the lower shaft 112. As discussed above, actuation of the primary trigger 104 will result in the rongeur 100 being in the illustrated closed position. FIG. 5 also illustrates a front portion of the rongeur 100. However, in the example of FIG. 5, the upper shaft 108 is at least in a partially open position, where the cutting blade 114 is separated from (not contacting) the static footplate 116. In addition, with the upper shaft 108 in the at least partially open position, the sliding footplate 118 is visible. In the example of FIG. 5, since the sliding footplate 118 is somewhat separated from (not contacting) the static footplate 118, the secondary trigger 106 may be at least partially actuated. The example of FIG. 5 also illustrates a surface 114A of the cutting blade 114, which is beveled inward (e.g., the perimeter of the leading edge of the cutting blade 114 being the narrow-most portion) to reduce the likelihood of jamming.

Figure 6:
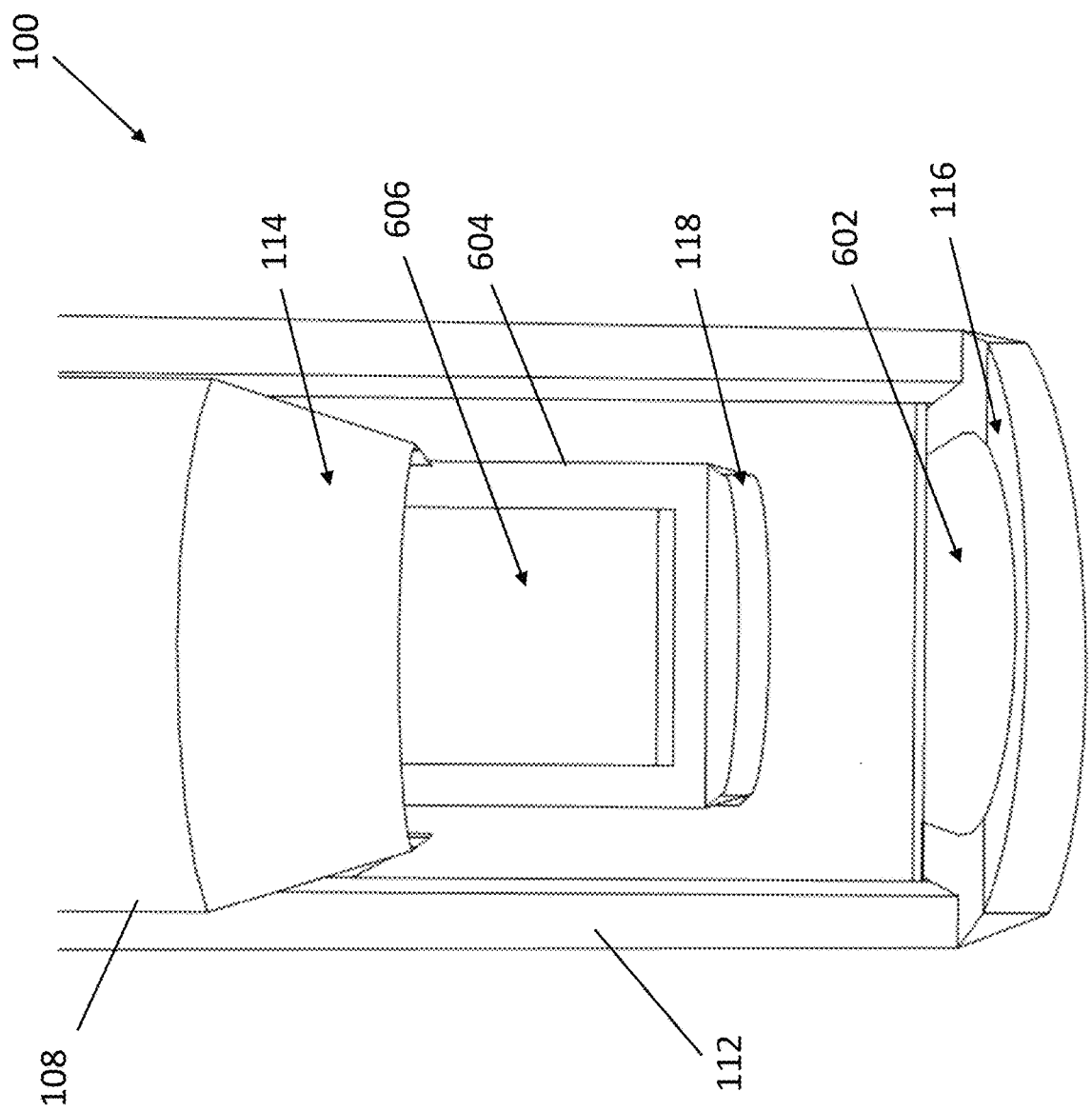
FIG. 6 illustrates a top-down view of a front portion of the rongeur of FIG. 1, in accordance with some embodiments.

Referring now to the example of FIG. 6, illustrated therein in a top-down view of a front portion of the rongeur 100. In particular, the top-down view of FIG. 6 illustrates the upper shaft 108 in an open position, where the cutting blade 114 is separated from (not contacting) the static footplate 116. The example of FIG. 6 also shows the sliding footplate 118 (in a partially retracted position, as controlled by the secondary trigger 106). In some embodiments, the static footplate 116 also includes a recess 602 configured to receive the sliding footplate 118 (e.g., while the secondary trigger 106 is not actuated). In addition, the example of FIG. 6 illustrates an elongated member 604 that is coupled to the secondary trigger 106 and which is slidably coupled along a floor of the lower shaft 112 of the rongeur 100. The elongated member 604 terminates in the sliding footplate 118 at the distal end of the elongated member 604. In various embodiments, the elongated member 604 includes an opening 606 proximate to the distal end of the elongated member 604, where the trap door is circumscribed within the opening 606, as discussed in more detail below.

Figure 7:
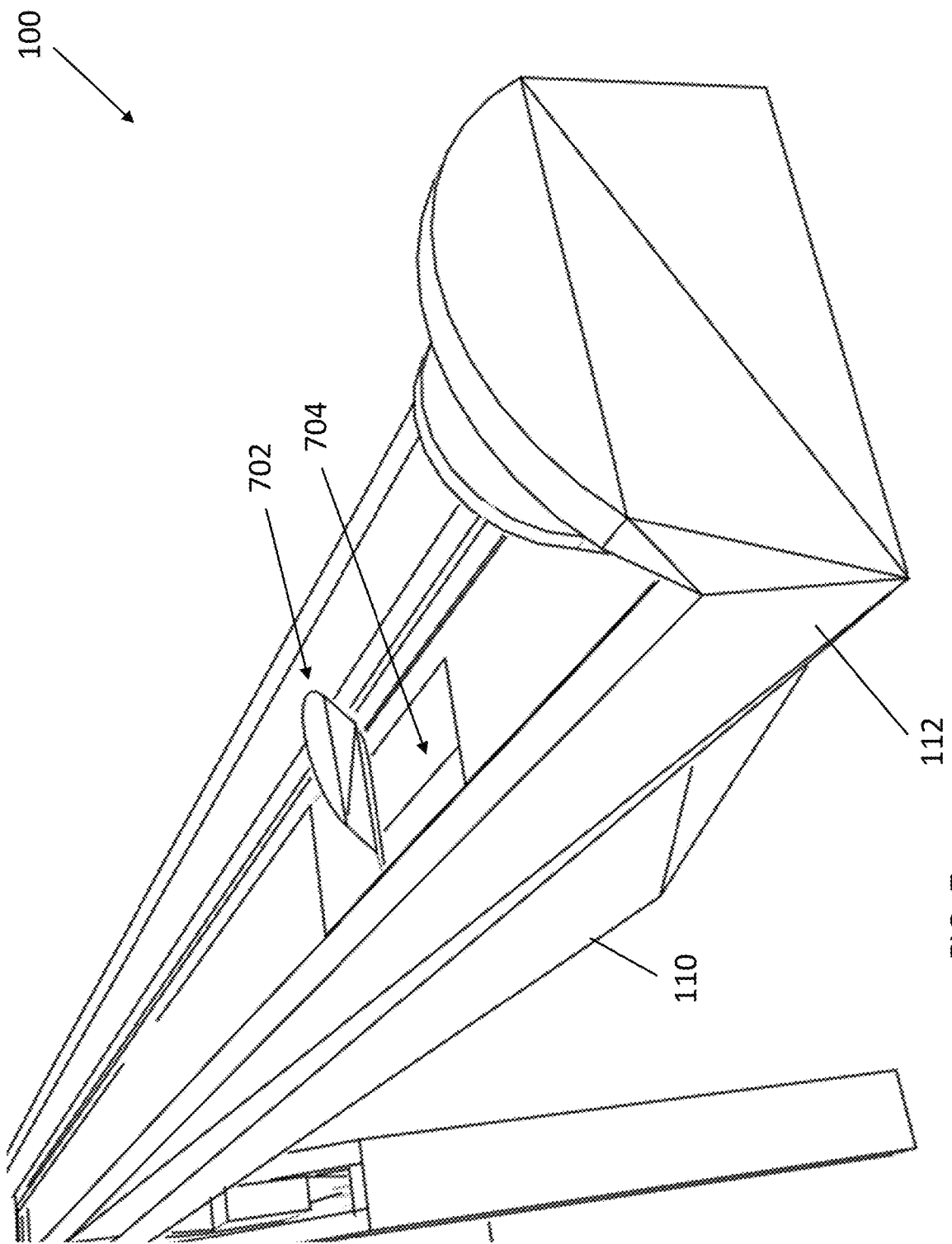
FIG. 7 illustrates another embodiment of the rongeur of FIG. 1, showing a trap door, in accordance with some embodiments.
Figure 8:
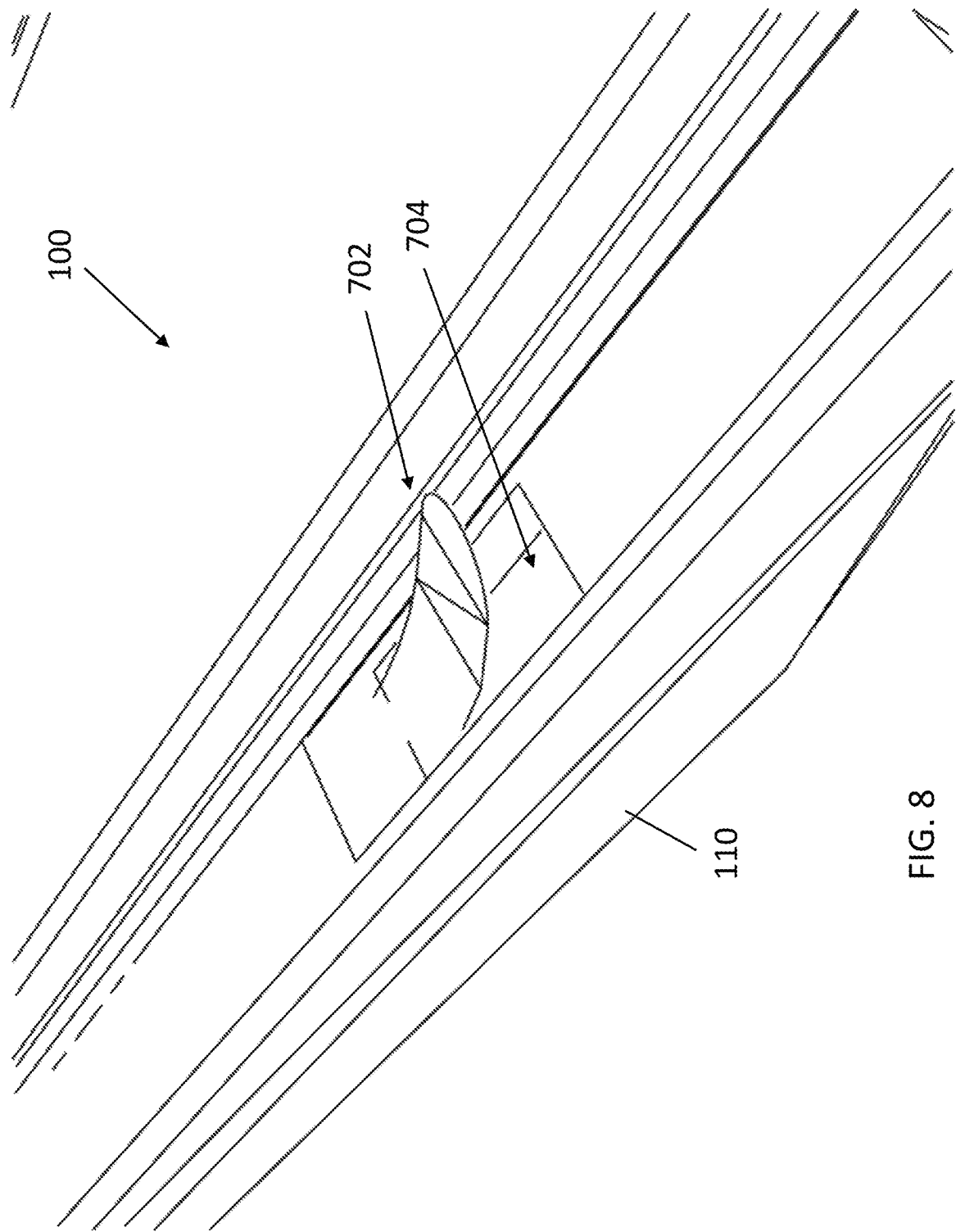
FIG. 8 illustrates still another embodiment of the rongeur of FIG. 1, showing the trap door, in accordance with some embodiments.

With reference to FIG. 7, illustrated therein is an embodiment of the rongeur 100 with the upper shaft 108 removed to reveal the trap door 702 that is used to prevent or provide access to the waste chamber 110, for example, depending on whether the upper shaft 108/cutting blade 114 is in the open or closed position. For example, as described in more detail below, the upper shaft 108 may include a crossbar coupled across a bottom portion of the upper shaft 108 such that the crossbar pushes down on the trap door 702, to close the trap door 702, when the upper shaft 108/cutting blade 114 is in the closed position. As shown in FIG. 7, when the trap door 702 is open (e.g., the upper shaft 108/cutting blade 114 being in the open position), an opening 704 in the floor of the bottom shaft 112 provides access to the waste chamber 110. In some embodiments, the trap door 702 may be equivalently referred to as a "spring valve". FIG. 8 shows an alternate view of the rongeur 100 with the upper shaft 108 removed such that the trap door 702 and the opening 704 are visible. Referring to FIGS. 9A and 9B, illustrated therein are additional views of the rongeur 100 illustrating an example of the actuation of the trap door 702. The upper shaft 108 is not shown here for clarity of discussion. Also, it is noted that rectangular prism 902, shown in FIGS. 9A and 9B, is a computer-aided design (CAD) artifact and is not a physical part of the as-fabricated rongeur 100. FIG. 9A illustrates the trap door 702 in an open position, which occurs when the upper shaft 108 is in the open position (e.g., when the primary trigger 104 is not actuated and the cutting blade 114 is not engaged with the static footplate 116). FIG. 9B illustrates the trap door 702 in a closed position, which occurs when the upper shaft 108 is in the closed position (e.g., when the primary trigger 104 is actuated and the cutting blade 114 is engaged with the static footplate 116). In some embodiments, closure of the trap door 702 may be facilitated by a crossbar (or other solid surface) disposed along a bottom portion of the upper shaft 108, as noted above, where the crossbar effectively blocks the trap door 702 in the closed position while the upper shaft 108 remains in the closed position. In some cases, the upper shaft 108 may alternatively have at least a partially solid bottom surface that effectively blocks the trap door 702 in the closed position.

FIGS. 9A and 9B also illustrate alternate views of the static footplate 116 including the recess 602 that receives the sliding footplate 118 (e.g., while the secondary trigger 106 is not actuated). Also shown is another view of the elongated member 604 that is coupled to the secondary trigger 106 and which is slidably coupled along the floor of the lower shaft 112. As discussed above, the elongated member 604 terminates in the sliding footplate 118 at the distal end of the elongated member 604, and the elongated member 604 includes the opening 606 proximate to the distal end of the elongated member 604, where the trap door 702 is circumscribed within the opening 606.

Figure 10:
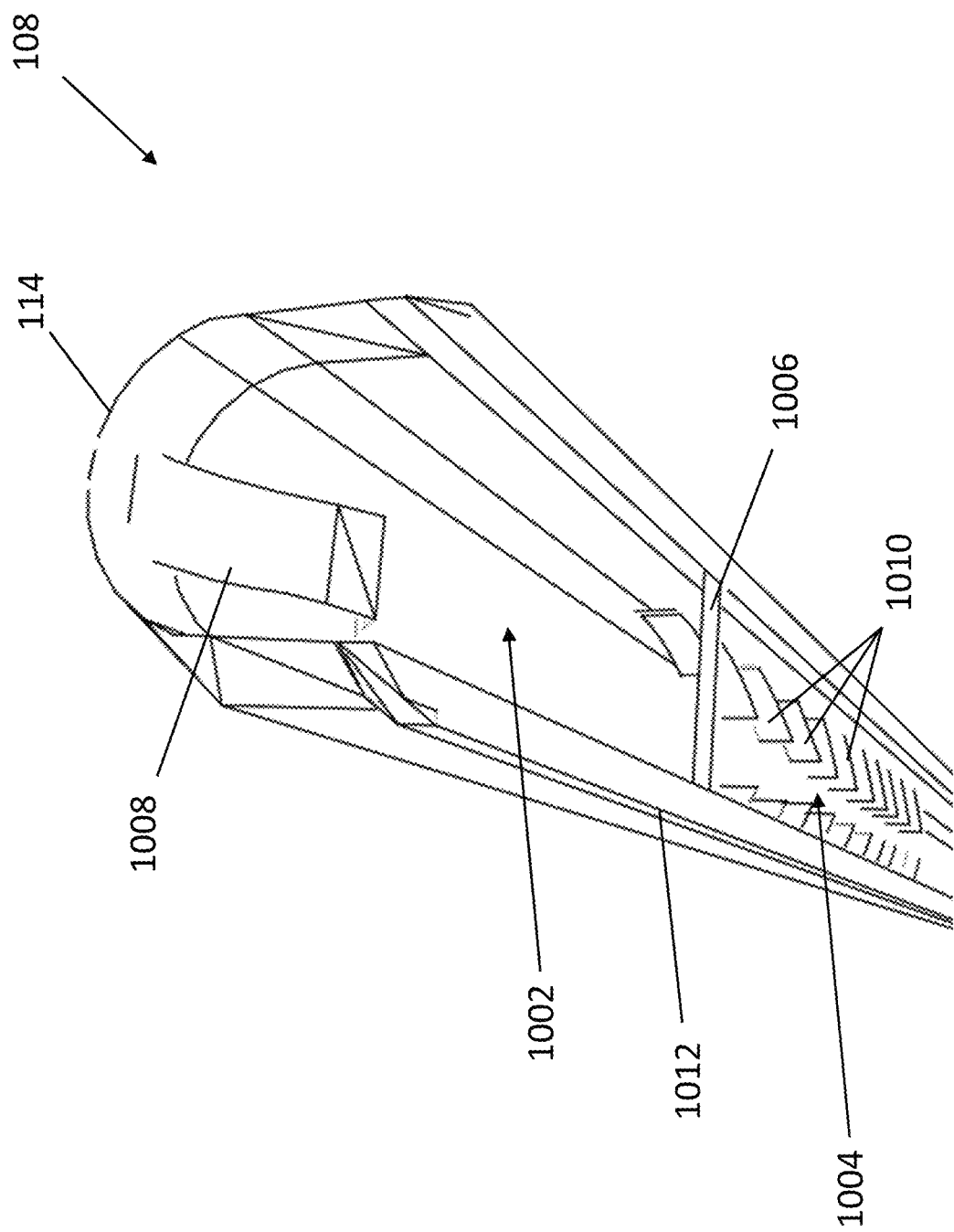
FIG. 10 and FIG. 11 illustrate bottom views of an upper shaft of the rongeur of FIG. 1, in accordance with some embodiments.
Figure 11:
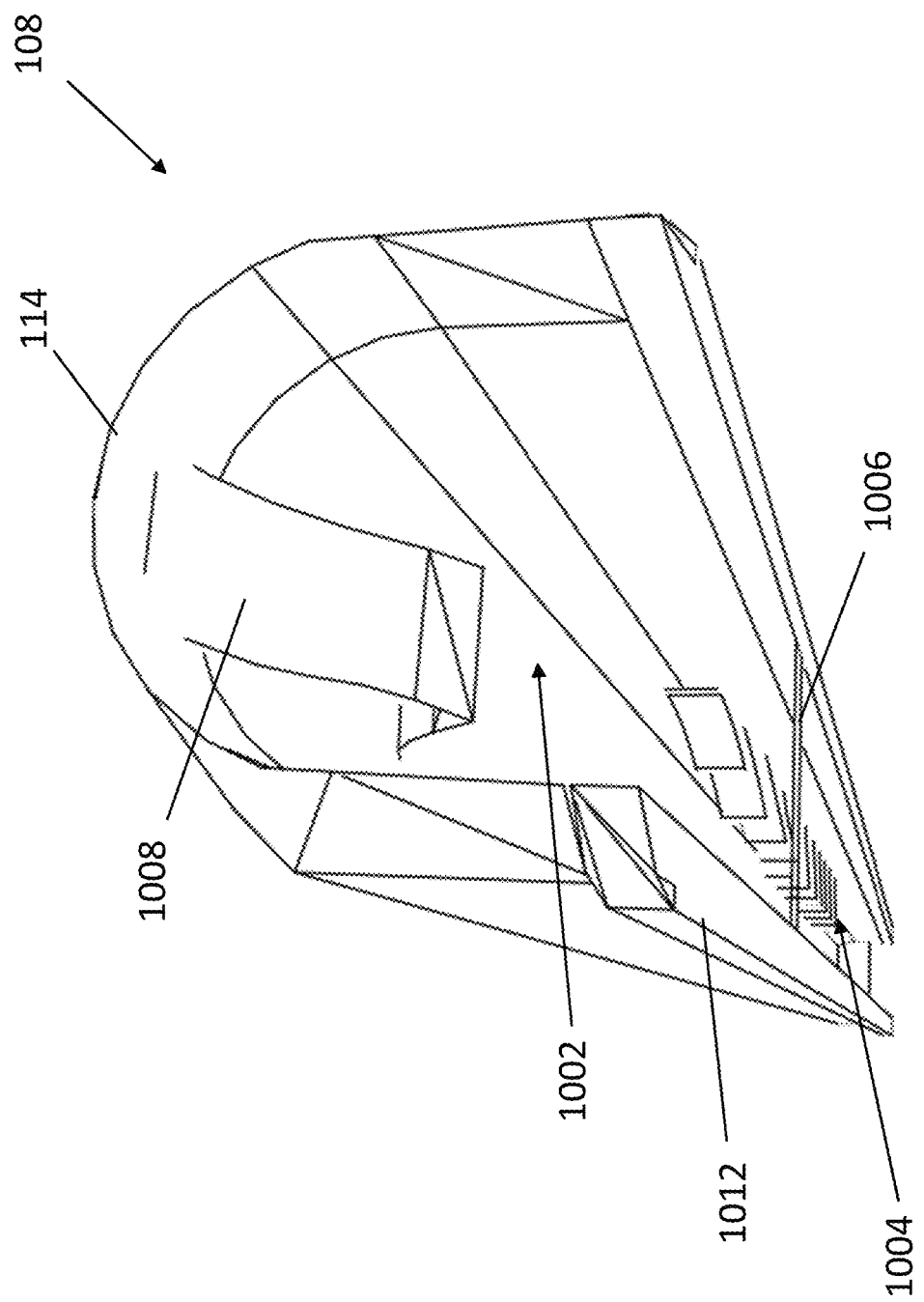

Referring now to FIG. 10, illustrated therein is a bottom view of the upper shaft 108 of the rongeur 100. In particular, the example of FIG. 10 illustrates a holding chamber 1002 defined within the upper shaft 108 proximate to the cutting blade 114. In some embodiments, the upper shaft 108 also includes a spring 1008 coupled to an upper interior surface of the upper shaft 108 within the holding chamber 1002. In some cases, the spring 1008 may assist with the forceful ejection of bite contents (e.g., that remain in the holding chamber 1002 and which were not otherwise selectively stored in a storage chamber 1004 by actuation of the secondary trigger 106) through the trap door 702 by pressure applied on the bite contents by the spring 1008 (e.g., upon release of the primary trigger 104). The example of FIG. 10 further illustrates the storage chamber 1004 defined within the upper shaft 108 proximate to the holding chamber 1002. In some embodiments, the storage chamber 1004 may also include semi-rigid teeth 1010 that serve to trap or store one or more of a plurality of bite contents therein. Also shown in FIG. 10 is a crossbar 1006 used to block the trap door 702 in the closed position (e.g., as shown in FIG. 9B) while the upper shaft 108 is in the closed position, as discussed above. In various examples, the upper shaft 108 may further include ridges 1012 along opposing outer bottom edges of the upper shaft 108, where the ridges 1012 are configured to engage with, or slidably couple to, corresponding grooves within the lower shaft 112. FIG. 11 shows an alternate bottom view of the upper shaft 108 illustrating the holding chamber 1002, the storage chamber 1004, the spring 1008, and the crossbar 1006, among other features also shown in FIG. 10.

Figure 12:
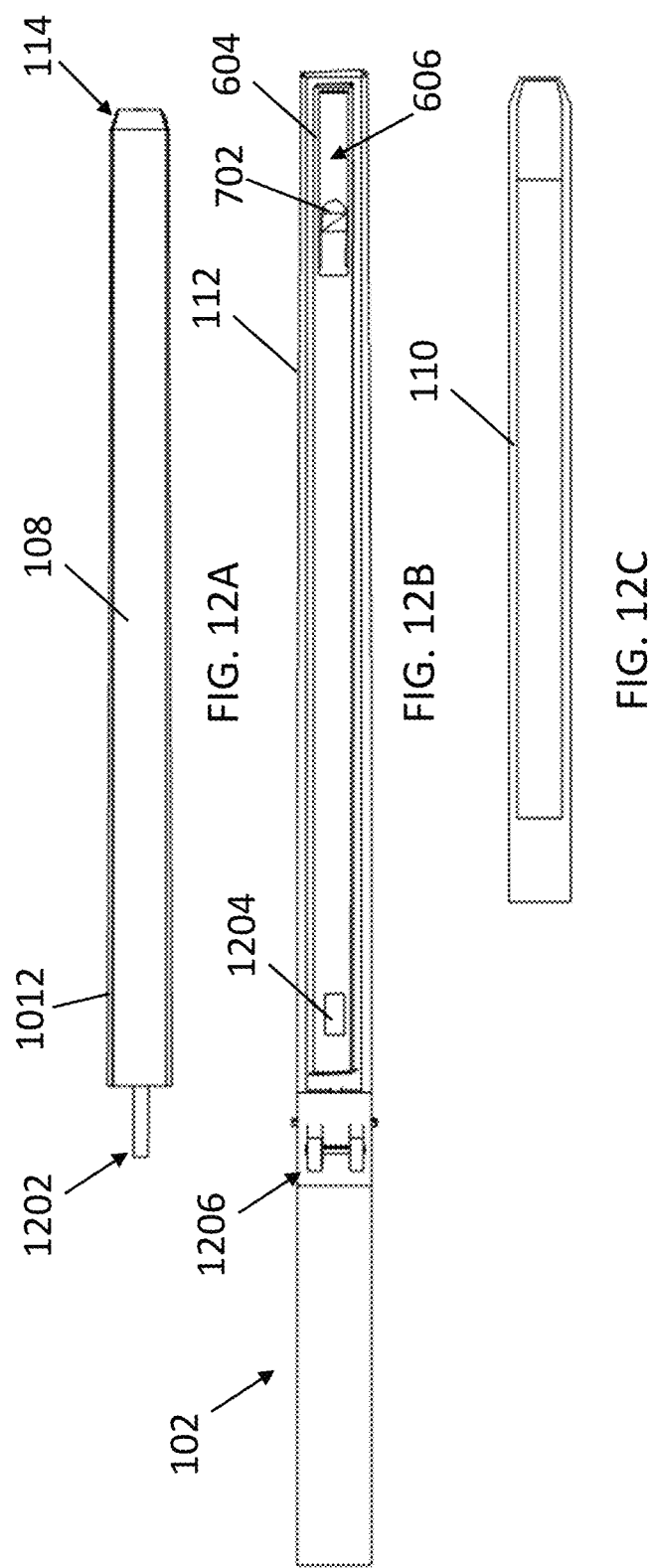
FIGS. 12A/12B/12C illustrate top-down views of the various components of the rongeur of FIG. 1, in accordance with various embodiments.

With reference now to FIGS. 12A/12B/12C, illustrated therein are top-down views of various components of a disassembled rongeur, such as the rongeur 100, in accordance with various embodiments. For example, FIG. 12A illustrates a top-down view of the upper shaft 108 including the cutting blade 114. The upper shaft 108 may also include the holding chamber 1002 and storage chamber 1004, among other components, as discussed above. In some embodiments, the upper shaft 108 also includes a coupling member 1202. In some examples, the coupling member 1202 may be configured to couple to an upper portion 1206 (FIG. 12B) of the primary trigger 104 (e.g., the upper portion 1206 of the primary trigger 104 inserted into and passing through a slot in the lower shaft 112) to provide actuation of the upper shaft 108 via the primary trigger 104. FIG. 12B illustrates a top-down view of the lower shaft 112, the handle 102, and the elongated member 604 that is slidably coupled along a floor of the lower shaft 112. In some embodiments, the lower shaft 112 and the handle 102 include a single, continuous piece of material. FIG. 12B also illustrates the opening 606 of the elongated member 604, where the trap door 702 is circumscribed within the opening 606. In some cases, the elongated member 604 is coupled to the secondary trigger 106 (e.g., at a coupling joint 1204) such that the secondary trigger 106 may actuate the sliding footplate 118 to selectively save or discard bite contents. Also shown in FIG. 12B is the upper portion 1206 of the primary trigger 104 configured for coupling to the coupling member 1202. FIG. 12C illustrates a top-down view of the waste chamber 110, which is accessible via the trap door 702, as described above.

Figure 13:
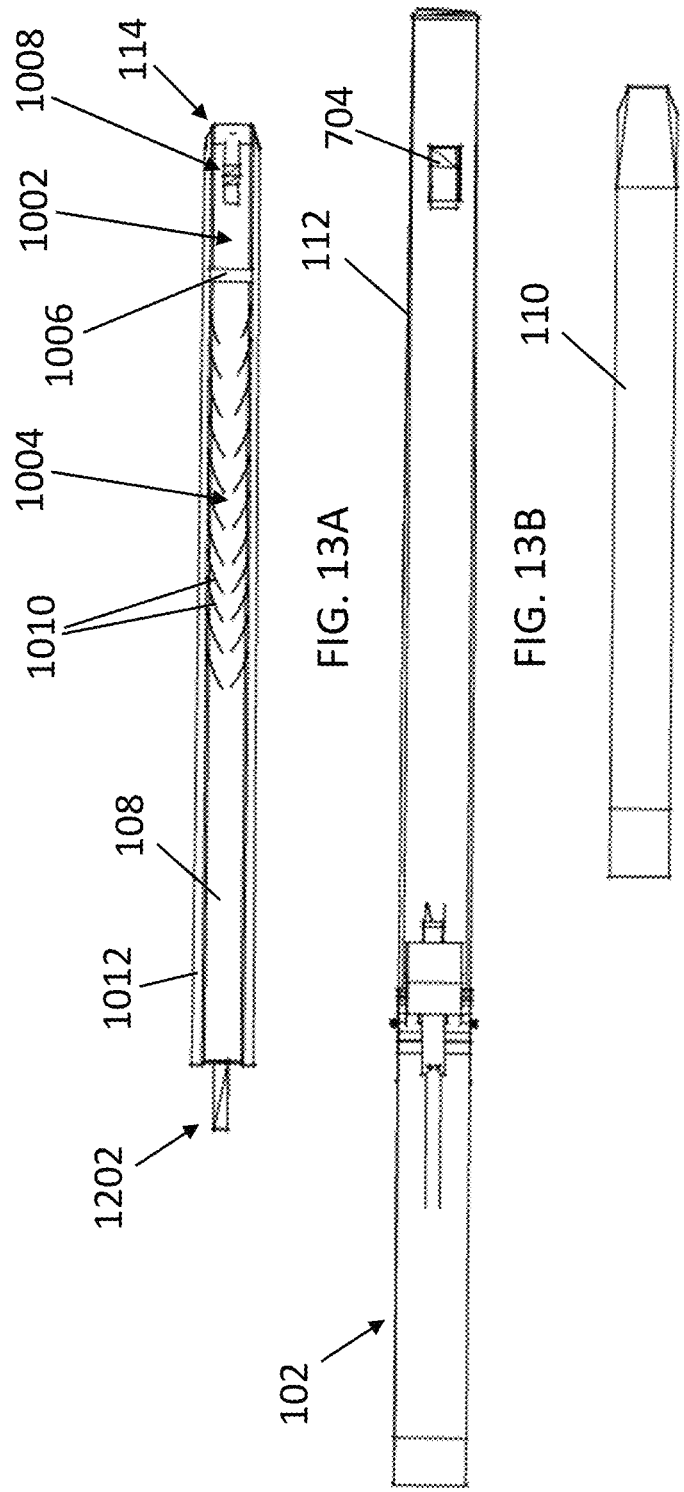
FIGS. 13A/13B/13C illustrate bottom-up views of the various components of the rongeur of FIG. 1, in accordance with various embodiments.

Referring to FIGS. 13A/13B/13C, illustrated therein are bottom-up views of various components of a disassembled rongeur, such as the rongeur 100, in accordance with various embodiments. For example, FIG. 13A illustrates a bottom-up view of the upper shaft 108 including the cutting blade 114, the holding chamber 1002, the storage chamber 1004, the crossbar 1006, the spring 1008, the semi-rigid teeth 1010, and the coupling member 1202. In some embodiments, and to reduce the likelihood of jamming, the storage chamber 1004 may gradually expand as one moves proximally away from the cutting blade 114. In some cases, the gradual expansion may begin at the holding chamber 1002 and continue through the storage chamber 1004 as one moves proximally away from the cutting blade 114. By way of example, the gradual expansion of the holding chamber 1002 and/or the storage chamber 1004 may be accomplished by varying a thickness of a wall of the upper shaft 108 that defines the holding chamber 1002 and/or the storage chamber 1004. In other words, in some embodiments, the thickness of the wall of the upper shaft 108 may become gradually thinner as one moves proximally away from the cutting blade 114. In some cases, an outer wall diameter, measured from outer surfaces of opposing sidewalls of the upper shaft 108, remains substantially uniform to provide for smooth sliding/coupling with the lower shaft 112 (e.g., via the ridges 1012). Further, an inner wall diameter, measured from inner surfaces of opposing sidewalls of the upper shaft 108, may increase as one moves proximally away from the cutting blade 114 (e.g., due to the thinning of the thickness of the wall of the upper shaft 108) to provide for the gradual expansion of the holding chamber 1002 and/or the storage chamber 1004. FIG. 13B illustrates a bottom-up view of the lower shaft 112, the handle 102, and the opening 704 in the floor of the bottom shaft 112 that provides access to the waste chamber 110 when the trap door 702 is open. FIG. 13C illustrates a bottom-up view of the waste chamber 110, which is accessible via the trap door 702 and the opening 704, as described above.

Figure 14:
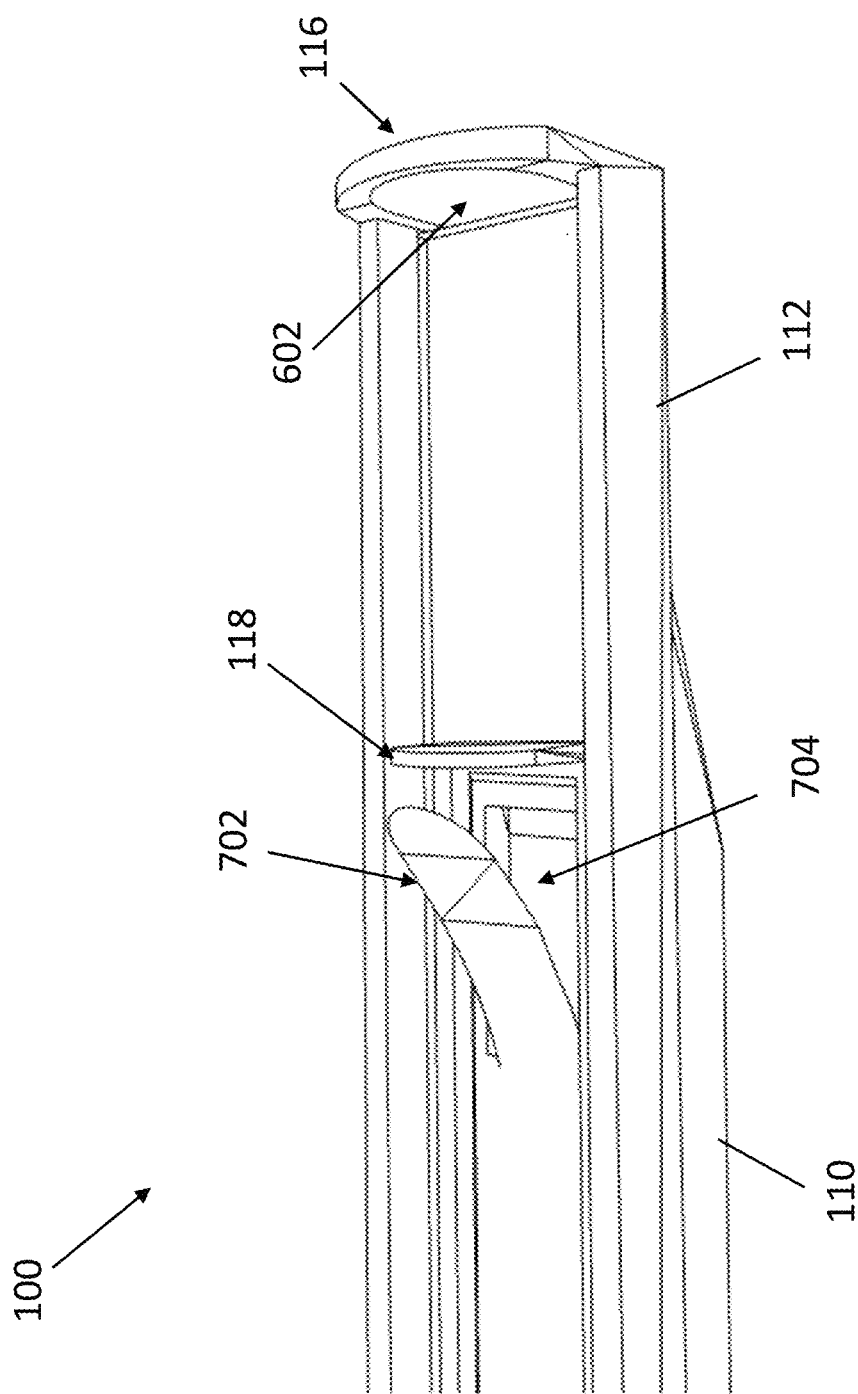
FIG. 14 and FIG. 15 illustrate exemplary views of the rongeur of FIG. 1 during a short pull and a long pull, respectively, in accordance with some embodiments.
Figure 15:
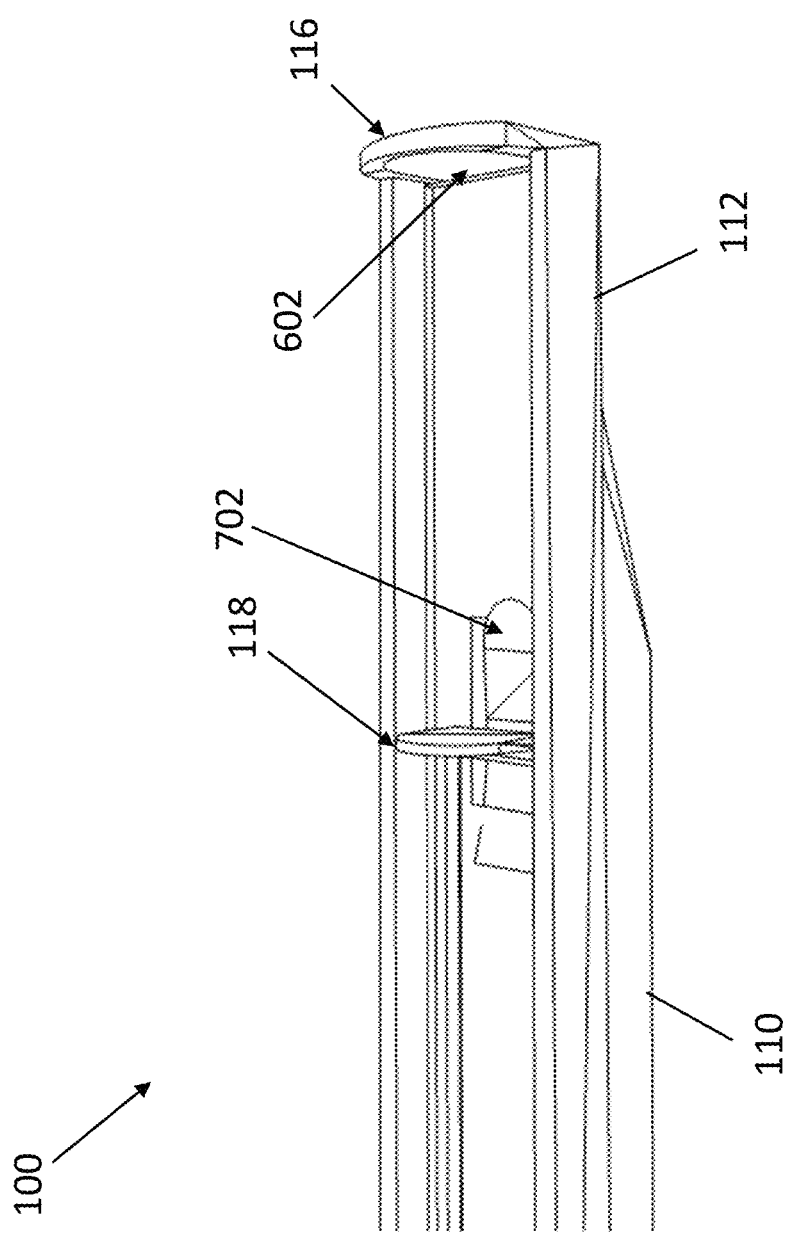

With reference now to FIGS. 14 and 15, illustrated therein are exemplary views of the rongeur 100 during a "short pull" (e.g., actuating the secondary trigger 106 into a first position) and a "long pull" (e.g., actuating the secondary trigger 106 into a second position), respectively. The upper shaft 108 is not shown here for clarity of discussion. As previously noted, while the primary trigger 104 is actuated (e.g., such that the cutting blade 114 bites bone or other material by contacting the static footplate 116), the secondary trigger 106 may be pulled into one of multiple positions (e.g., the first position or the second position) to selectively save or discard the bite contents. For example, pulling the secondary trigger 106 into the first position (short pull) may retract the sliding footplate 118 away from the static footplate 116 such that the sliding footplate 118 pushes the bite contents into the holding chamber 1002. In another example, pulling the secondary trigger 106 into a second position (long pull) may retract the sliding footplate 118 away from the static footplate 116 such that the sliding footplate 118 pushes the bite contents past the holding chamber 1002 and into the storage chamber 1004, where the bite contents are trapped or stored by the semi-rigid teeth 1010.

In some embodiments, when the primary trigger 104 is released and the upper shaft 108 slides back to its open position, the open trap door 702 obstructs the path through the upper shaft 108 (leading toward the storage chamber 1004) and instead bite contents present within the holding chamber 1002 are ejected from the holding chamber 1002 through the opening 704 that is accessible due to the open trap door 702. In some embodiments, the bite contents fall freely out of the opening 704 upon releasing the primary trigger 104. However, in some cases, the bite contents are forcefully ejected through the opening 704 by pressure applied on the bite contents by the spring 1008, as discussed above. Alternatively, in some embodiments and after releasing the primary trigger 104, the secondary trigger 106 may again be short pulled (e.g., actuated into the first position) in order to forcefully eject the bite contents, with the assistance of the sliding footplate 118, through the opening 704 accessible because of the open trap door 702.

It is noted that in the example of FIG. 14, the trap door 702 is illustrated as being open. Thus, in the example of FIG. 14 the primary trigger 104 is not actuated and the upper shaft 108 is in its open position. FIG. 14 may therefore illustrate the example where the secondary trigger 106 is again short pulled in order to forcefully eject (through the opening 704) bite contents from the holding chamber 1002 with the assistance of the sliding footplate 118. In the example of FIG. 15, the trap door 702 is illustrated as being closed. Thus, in the example of FIG. 15 the primary trigger 104 is actuated and the upper shaft 108 is in its closed position. To be sure, the secondary trigger 106 may only be long pulled when the upper shaft 108 is in the closed position. Otherwise, if the upper shaft 108 is in the open position, the trap door 702 will be open, thus obstructing the path leading toward the storage chamber 1004 (similar to the example of FIG. 14). In some embodiments, the lower shaft 112 may include one or more catches, tabs, or other features designed to catch the sliding footplate 118, and which may require additional pulling force to overcome the catch, to enable a user to quickly distinguish a short pull from a long pull and/or to prevent a long pull when a short pull is desired.

Figure 16:
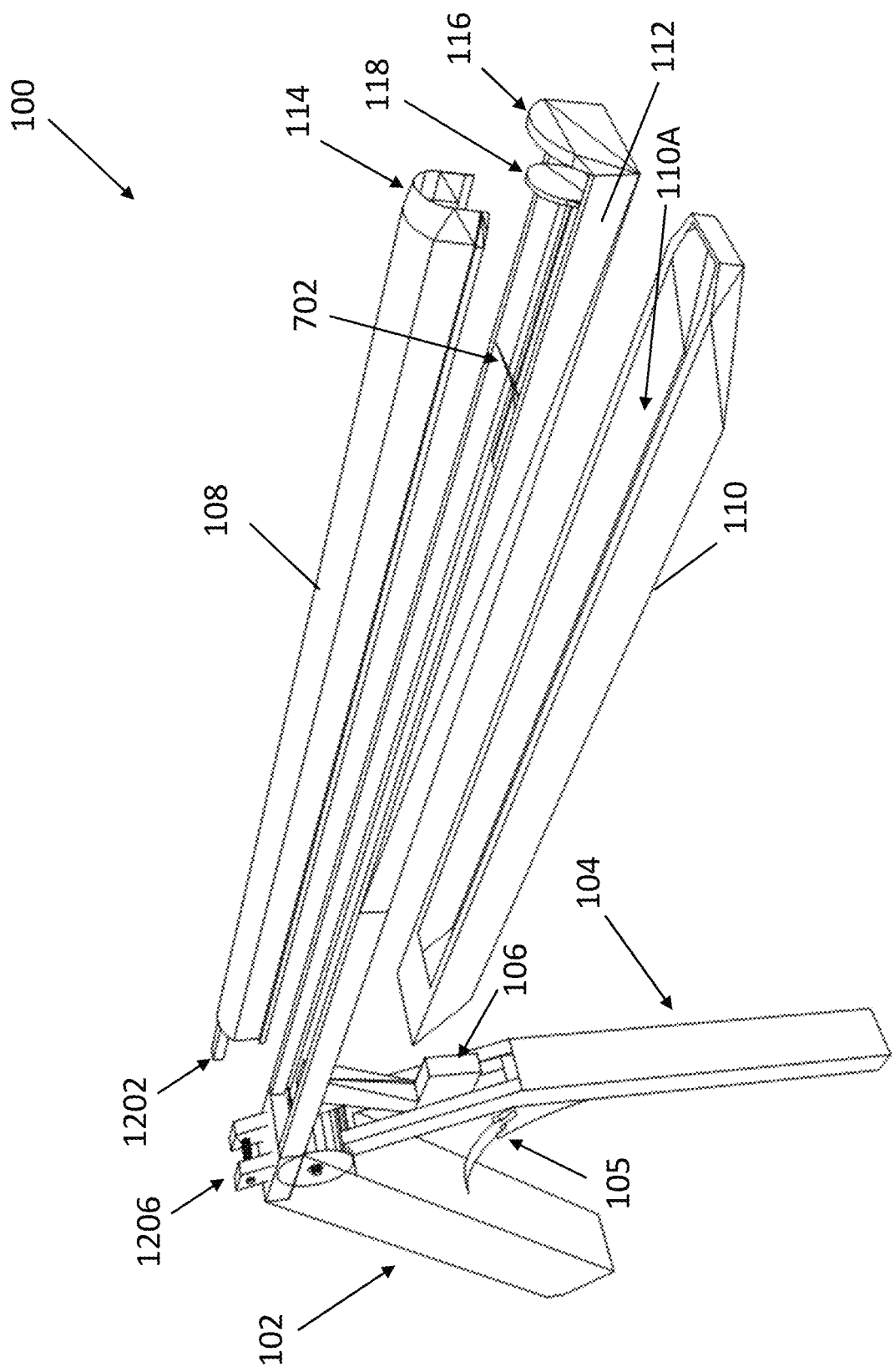
FIGS. 16, 17, and 18 illustrate perspective views of a disassembled rongeur, such as the rongeur of FIG. 1, in accordance with various embodiments.
Figure 17:
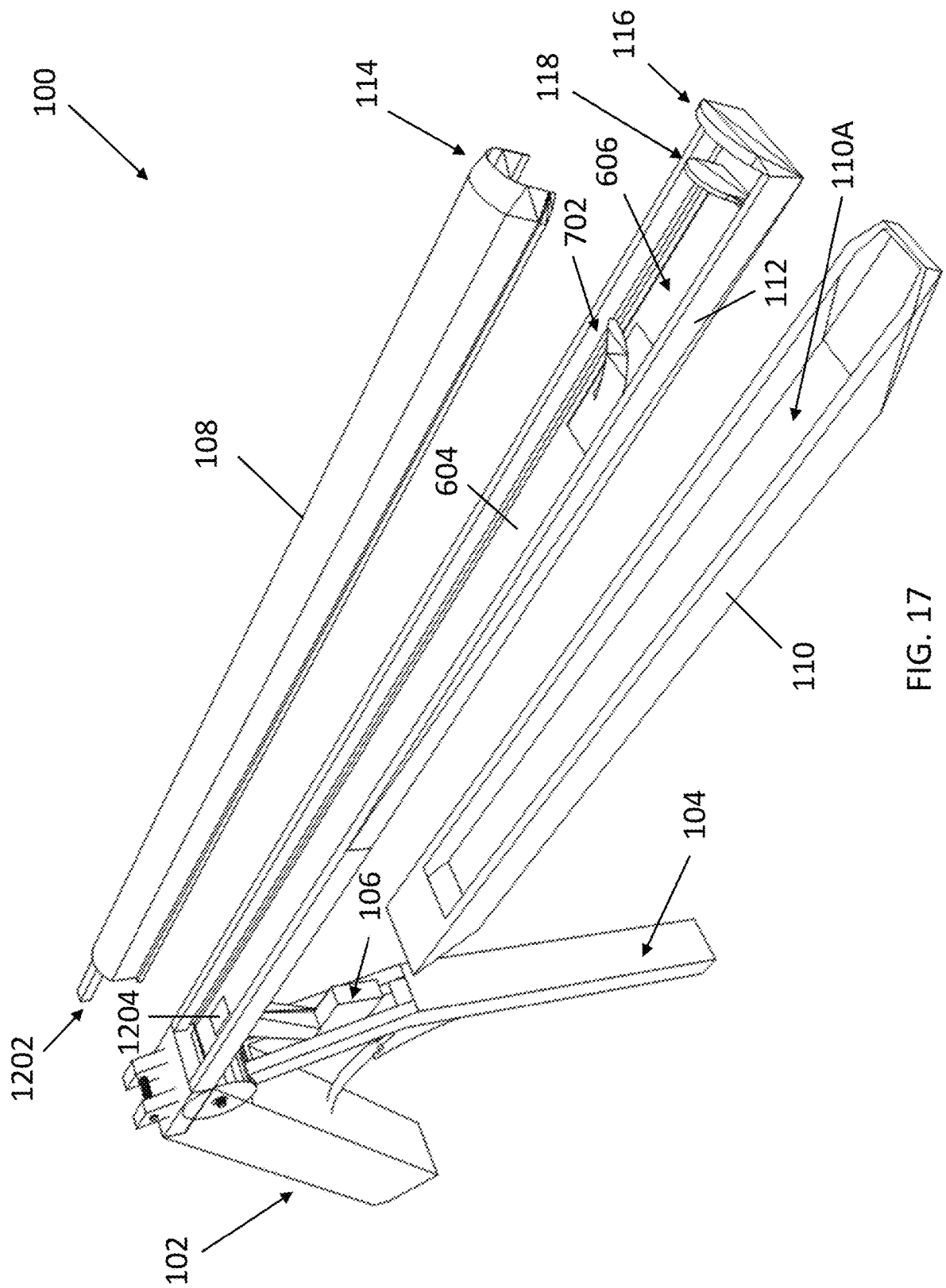
Figure 18:
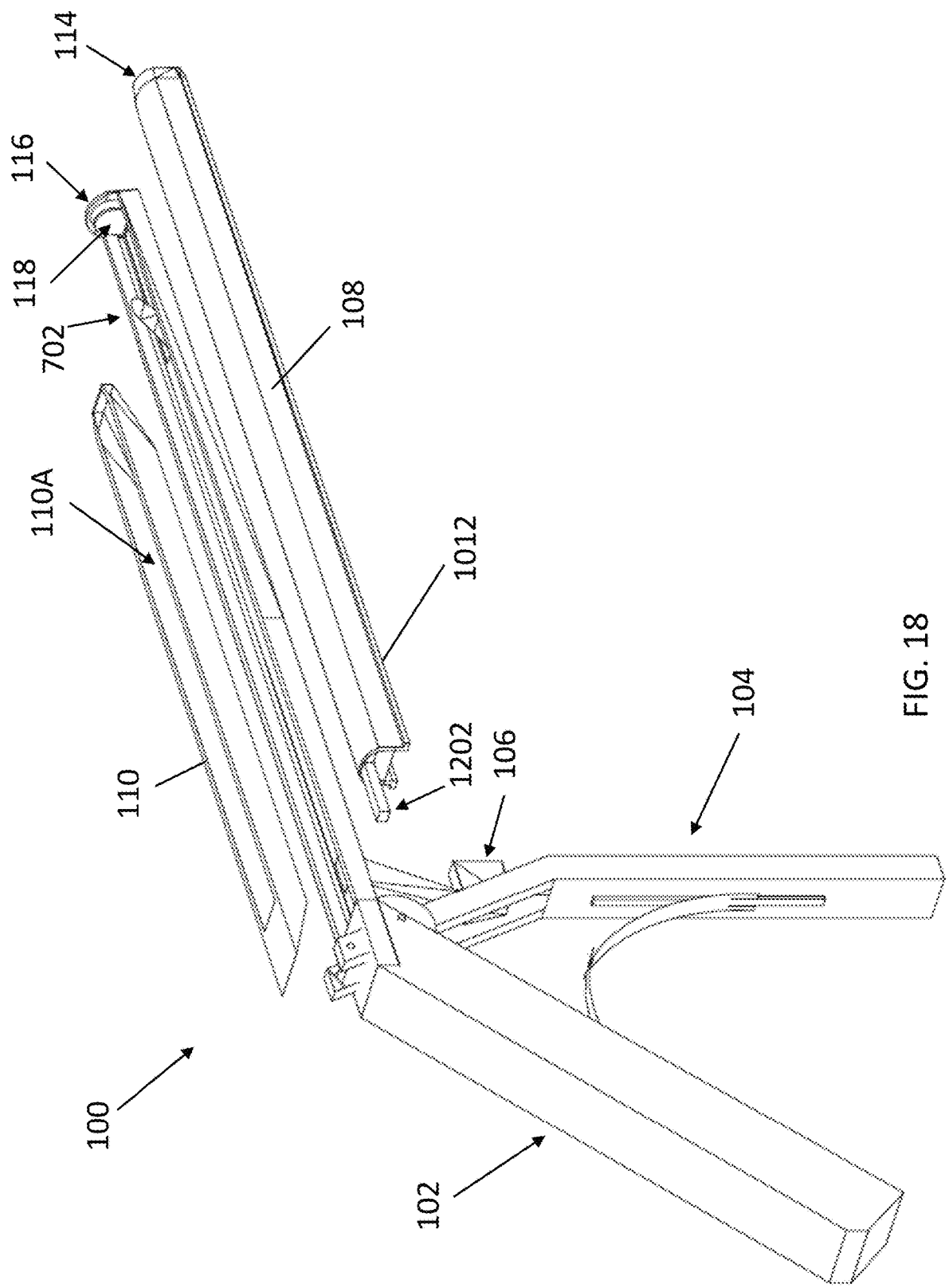

The examples of FIGS. 16, 17, and 18 illustrate a variety of perspective views of embodiments of a disassembled rongeur, such as the rongeur 100, the features of which have been largely described above. FIGS. 16, 17, and 18, however, do provide better views of a cavity 110A of the waste chamber 110, into which discarded bite contents may be ejected (e.g., until the cavity 110A is full). In some embodiments, the cavity 110A may have sloped surfaces near the front and rear of the cavity 110A, as shown. FIG. 17 also provides another view of the elongated member 604, coupled to the secondary trigger 106 (e.g., at the coupling joint 1204), and the opening 606 proximate to the distal end of the elongated member 604, with the trap door 702 circumscribed within the opening 606. In some embodiments, and besides the opening 606, the elongated member 604 may have a generally solid surface (e.g., in a region of the elongated member 604 between the coupling joint 1204 and the opening 606), as shown.

With respect to the description provided herein, the present disclosure provides an improved surgical rongeur and related method that effectively addresses the shortcomings of existing rongeurs. In various embodiments, the disclosed surgical rongeur provides for selectively saving or discarding bites of bone or other material. By way of example, and in addition to the primary trigger that actuates the upper shaft and distal cutting blade, the various embodiments also include a secondary trigger coupled to an elongated member slidably coupled along a floor of the lower shaft of the rongeur. The elongated member terminates in a sliding footplate at the distal end of the elongated member. In some embodiments, the static footplate of the lower shaft includes a recess configured to receive the sliding footplate (e.g., while the secondary trigger is not actuated). In some examples, and while the primary trigger is actuated (e.g., such that the cutting blade bites bone or other material by contacting the static footplate), the secondary trigger may be pulled into one of multiple positions to selectively save or discard the bite contents. The disclosed embodiments thus provide for safer, more effective, and less time-consuming surgical procedures, for example, as compared to at least some existing rongeur implementations. Those skilled in the art will recognize other benefits and advantages of the methods and surgical rongeur as described herein, and the embodiments described are not meant to be limiting beyond what is specifically recited in the claims that follow.

Thus, one of the embodiments of the present disclosure described a surgical rongeur including a lower shaft having a proximal end and a distal end, where the lower shaft defines a floor including a trap door disposed proximate to the distal end of the lower shaft, and where the lower shaft terminates in a static footplate at the distal end of the lower shaft. In some embodiments, the surgical rongeur further includes an upper shaft having a proximal end and a distal end, where the upper shaft is slidably coupled to a top surface of the lower shaft, and where the upper shaft terminates in a cutting blade at the distal end of the upper shaft. In some examples, the surgical rongeur further includes an elongated member slidably coupled along the floor of the lower shaft, where the elongated member has a proximal end and a distal end, and where the elongated member terminates in a sliding footplate at the distal end of the elongated member. In some cases, the surgical rongeur further includes a primary trigger coupled to the proximal end of the upper shaft, where actuation of the primary trigger is configured to alternately move the cutting blade between an open position and a closed position. In some embodiments, the surgical rongeur further includes a secondary trigger coupled to the proximal end of the elongated member, where actuation of the secondary trigger, while the cutting blade is in the closed position, is configured to retract the sliding footplate from the static footplate into one of a plurality of positions.

In another of the embodiments, discussed is a dual-chamber rongeur for selectively saving or discarding human tissue including a main body portion having a first footplate at a distal end of the main body portion and an actuatable valve disposed proximate to the first footplate. In some embodiments, the dual-chamber rongeur further includes a first chamber slidably coupled to a top surface of the main body portion, the first chamber further coupled to a first trigger adapted to move the first chamber into and out of a cutting position. In some examples, the dual-chamber rongeur further includes a second chamber coupled to a bottom surface of the main body portion and a second footplate slidably coupled within the main body portion. In some embodiments, the second footplate is further coupled to a second trigger adapted to move the second footplate into one of a plurality of position to perform the selectively saving or discarding the human tissue.

In yet another of the embodiments, discussed is method including providing a rongeur including a lower shaft having a static footplate at a distal end of the lower shaft, the lower shaft defining a floor including a trap door disposed proximate to the distal end of the lower shaft. In some embodiments, the rongeur further includes an upper shaft including a cutting blade at a distal end of the upper shaft, the upper shaft slidably coupled to a top surface of the lower shaft. In some cases, the rongeur further includes a waste chamber coupled to a bottom surface of the lower shaft and a sliding member slidably coupled along the floor of the lower shaft, the sliding member including a sliding footplate at a distal end of the sliding member. In some embodiments, the rongeur further includes a primary trigger coupled to a proximal end of the upper shaft and a secondary trigger coupled to a proximal end of the sliding member. In various embodiments, the method further includes actuating the primary trigger to move the cutting blade into a closed position to cut out a tissue sample. In some embodiments, the method further includes while the cutting blade is in the closed position, actuating the secondary trigger to retract the sliding footplate into a first position to discard the tissue sample or into a second position to save the tissue sample.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A surgical rongeur, comprising:
 a lower shaft having a proximal end and a distal end, wherein the lower shaft defines a floor including a trap door disposed proximate to the distal end of the lower shaft, and wherein the lower shaft terminates in a static footplate at the distal end of the lower shaft;
 an upper shaft having a proximal end and a distal end, the upper shaft slidably coupled to a top surface of the lower shaft, wherein the upper shaft terminates in a cutting blade at the distal end of the upper shaft;
 an elongated member slidably coupled along the floor of the lower shaft, the elongated member having a proximal end and a distal end, wherein the elongated member terminates in a sliding footplate at the distal end of the elongated member;
 a primary trigger coupled to the proximal end of the upper shaft, wherein actuation of the primary trigger is configured to alternately move the cutting blade between an open position and a closed position; and
 a secondary trigger coupled to the proximal end of the elongated member, wherein actuation of the secondary trigger, while the cutting blade is in the closed position, is configured to retract the sliding footplate from the static footplate into one of a plurality of positions.

2. The surgical rongeur of claim 1, wherein the static footplate includes a recess, and wherein the recess is configured to receive the sliding footplate.

3. The surgical rongeur of claim 1, wherein the elongated member includes an opening proximate to the distal end of the elongated member, and wherein the trap door is circumscribed within the opening.

4. The surgical rongeur of claim 1, wherein the upper shaft defines a holding chamber proximate to the cutting blade and a storage chamber proximate to the holding chamber.

5. The surgical rongeur of claim 4, wherein retraction of the sliding footplate into a first one of the plurality of positions is configured to move a material sample into the holding chamber.

6. The surgical rongeur of claim 5, wherein retraction of the sliding footplate into a second one of the plurality of positions is configured to move the material sample into the storage chamber.

7. The surgical rongeur of claim 1, further comprising:
 a waste chamber coupled to a bottom surface of the lower shaft.

8. The surgical rongeur of claim 7, wherein while the cutting blade is in the closed position the trap door remains closed to prevent access to the waste chamber.

9. The surgical rongeur of claim 7, wherein while the cutting blade is in the open position the trap door remains open to provide access to the waste chamber.

10. The surgical rongeur of claim 1, further comprising:
 a spring coupled to an upper interior surface of the upper shaft within a holding chamber defined by the upper shaft, wherein the spring is configured to, while the cutting blade transitions from the closed position to the open position, eject a material sample from within the holding chamber through the trap door.

11. A dual-chamber rongeur for selectively saving or discarding human tissue, comprising:
 a main body portion having a first footplate at a distal end of the main body portion and an actuatable valve disposed proximate to the first footplate;
 a first chamber slidably coupled to a top surface of the main body portion, the first chamber further coupled to a first trigger adapted to move the first chamber into and out of a cutting position;
 a second chamber coupled to a bottom surface of the main body portion; and
 a second footplate slidably coupled within the main body portion, the second footplate further coupled to a second trigger adapted to move the second footplate into one of a plurality of positions to perform the selectively saving or discarding the human tissue.

12. The dual-chamber rongeur of claim 11, wherein the actuatable valve provides an opening within the main body portion to provide access to the second chamber.

13. The dual-chamber rongeur of claim 11, wherein the first chamber includes a cutting blade at a distal end of the first chamber, a holding chamber proximate to the cutting blade, and a storage chamber proximate to the holding chamber.

14. The dual-chamber rongeur of claim 11, wherein the second chamber includes a waste chamber.

15. The dual-chamber rongeur of claim 11, wherein the second trigger is adapted to, while the first chamber is in the cutting position, move the second footplate into a first one of the plurality of positions to discard the human tissue.

16. The dual-chamber rongeur of claim 15, wherein the second trigger is adapted to, while the first chamber is out of the cutting position, move the second footplate into a second one of the plurality of positions to save the human tissue.

17. The dual-chamber rongeur of claim 11, further comprising:
 a spring coupled to an upper interior surface of the first chamber, wherein the spring is configured to, while the first chamber transitions out of the cutting position, eject the human tissue into the second chamber via the actuatable valve.

18. A method, comprising:
 providing a rongeur, wherein the rongeur comprises:
  a lower shaft including a static footplate at a distal end of the lower shaft, the lower shaft defining a floor including a trap door disposed proximate to the distal end of the lower shaft;
  an upper shaft including a cutting blade at a distal end of the upper shaft, the upper shaft slidably coupled to a top surface of the lower shaft;
  a waste chamber coupled to a bottom surface of the lower shaft;
  a sliding member slidably coupled along the floor of the lower shaft, the sliding member including a sliding footplate at a distal end of the sliding member;
  a primary trigger coupled to a proximal end of the upper shaft; and a secondary trigger coupled to a proximal end of the sliding member;

actuating the primary trigger to move the cutting blade into a closed position to cut out a tissue sample; and while the cutting blade is in the closed position, actuating the secondary trigger to retract the sliding footplate into a first position to discard the tissue sample or into a second position to save the tissue sample.

19. The method of claim 18, wherein the actuating the secondary trigger to retract the sliding footplate into the first position moves the tissue sample into a holding chamber defined by the upper shaft, and wherein upon returning the cutting blade into an open position, the tissue sample within the holding chamber is ejected into the waste chamber.

20. The method of claim 18, wherein the actuating the secondary trigger to retract the sliding footplate into the second position moves the tissue sample into a storage chamber defined by the upper shaft, and wherein upon returning the cutting blade into an open position, the tissue sample remains in the storage chamber.

\* \* \* \* \*